United States Patent [19]
Kimoto et al.

[11] Patent Number: 6,001,618
[45] Date of Patent: Dec. 14, 1999

[54] HALOACETOACETATE REDUCTASE, METHOD FOR PRODUCING SAID ENZYME, AND METHOD FOR PRODUCING ALCOHOLS USING SAID ENZYME

[75] Inventors: Norihiro Kimoto; Hiroaki Yamamoto, both of Ibaraki, Japan

[73] Assignee: Daicel Chemical Industries, Ltd., Japan

[21] Appl. No.: 09/219,179

[22] Filed: Dec. 22, 1998

[30] Foreign Application Priority Data

Dec. 25, 1997 [JP] Japan ..................................... 9-357969

[51] Int. Cl.$^6$ ................................ C12N 9/06; C12P 7/62
[52] U.S. Cl. ......................... 435/191; 435/71.1; 435/135; 435/280
[58] Field of Search ..................................... 435/135, 280, 435/191, 71.1

[56] References Cited

U.S. PATENT DOCUMENTS

| | | | |
|---|---|---|---|
| 5,413,921 | 5/1995 | Onishi et al. | 435/135 |
| 5,559,030 | 9/1996 | Matsuyama et al. | 435/280 |
| 5,780,649 | 7/1998 | Yuasa et al. | 549/313 |
| 5,891,685 | 4/1999 | Yamagishi et al. | 435/135 |

FOREIGN PATENT DOCUMENTS 61-146191  7/1986  Japan .

OTHER PUBLICATIONS

Heidlas et al., "Purification and Characterization of two Oxidoreductases Involved in the Enantioselective Reduction of 3–oxo, 4–oxo and 5–oxo Esters in Baker's Yeast", Eur. J. Biochem. 172:633–639, 1988.

Kataoka et al., "A Novel NADPH–Dependent Carbonyl Reductase of *Candida Macedoniensis*: Purification and Characterization", Archives of Biochemistry and Biophysics 294:469–474, 1992.

Nakamura et al., "Stereochemical Control of Microbial Reduction. 17. A Method for Controlling the Enantioselectivity of Reductions with Bakers' Yeast", J. Org. Chem. 56:4778–4783, 1991.

Patel et al., "Stereoselective Reduction of β–Keto Esters by *Geotrichum Candidum*", Enzyme Microb. Technol. 14:731–738, 1992.

Shieh et al., "Stereochemical Control of Yeast Reductions. 5. Characterization of the OxidoreductasesInvolved in the Reduction of β–Keto Esters", J. Am. Chem. Soc. 107:2993–2994, 1995.

*Primary Examiner*—Herbert J. Lilling
*Attorney, Agent, or Firm*—Fish & Richardson P.C.

[57] ABSTRACT

A novel enzyme is provided. This enzyme is capable of reducing 4-haloacetoacetic acid esters to produce (S)-4-halo-3-hydroxybutyric acid esters with high optical purity. The enzyme was isolated from a microorganism belonging to the genus Kluyveromyces. Using the enzyme, (S)-4-halo-3-hydroxybutyric acid esters, which are useful as HMG-CoA reductase inhibitors, intermediates for synthesizing various medicines and agricultural chemicals, can be efficiently produced with high optical purity.

5 Claims, 3 Drawing Sheets

HALOACETOACETATE REDUCTASE, METHOD FOR PRODUCING SAID ENZYME, AND METHOD FOR PRODUCING ALCOHOLS USING SAID ENZYME

FIELD OF THE INVENTION

The present invention relates to a novel ketone reductase, a method for preparing the said enzyme, and a method for producing alcohols, especially (S)-4-halo-3-hydroxybutyric acid esters using the said enzyme.

BACKGROUND OF THE INVENTION (S)-4-Halo-3-acetoacetic acid esters are important as HMG-CoA reductase inhibitors and intermediates for synthesizing various medicines and agricultural chemicals such as D-carnitine. The known methods for producing optically active 4-halo-3-hydroxybutyric acid esters include the asymmetric reduction methods using 3α-hydroxysteroid dehydrogenase (Japanese Patent Laid-Open Publication (JP-A) No. Hei 1-1277494) or bakers' yeast (J. Am. Chem. Soc. 105, 5925–5926 (1983), and JP-A-Sho 61-146191).

Furthermore, the known methods for reducing 4-haloacetoacetic acid esters to produce 4-halo-3-hydroxybutyric acid esters include methods using enzymes such as *Saccharomyces cerevisiae*-derived D-enzyme-1 and D-enzyme-2 (J. Org. Chem. 56, 4778–4783 (1991)), L-enzyme-1 and L-enzyme-2 (Biosci. Biotech. Biochem. 58, 2236–2240 (1994)), aldehyde reductase derived from *Sporobolomyces salmonicolor* (Biochim. Biophys. Acta 1122, 57–62 (1992)), aldehyde reductase derived from Sporobolomyces sp. (Biosci. Biotech. Biochem. 57, 303–307 (1993)), aldehyde reductase derived from *Candida alcabins* (Biosci. Biotech. Biochem. 57, 303–307 (1993)), aldehyde reductase derived from *Trichosporon fermentans* (JP-A-Hei08-126487 (960521)), aldehyde reductase derived from *Hansenula mrakii* (JP-A-Hei08-126486 (960521)), ethyl ketopantothenate reductase derived from *Candida macedoniensis* (Arch. Biochem. Biophys. 294, 469–474 (1992)), and ethyl 4-chloroacetoacetate reductase derived from *Geotrichum candidum* (Enzyme Microb. Technol. 14, 731–738 (1992)). Among these methods, those using ethyl ketopantothenate reductase derived from *Candida macedoniensis*, D-enzyme-1 and D-enzyme-2 derived from *Saccharomyces cerevisiae*, and ethyl 4-chloroacetoacetate reductase derived from *Geotrichum candidum* produce the (S)-enatiomer of 4-halo-3-hydroxybutyric acid esters. However, these methods for producing (S)-4-halo-3-hydroxybutyric acid esters have the disadvantages of low optical purity and product yield.

The present inventors found that microorganisms including the genus Kluyveromyces reduce 4-haloacetoacetic acid esters to produce optically active 4-halo-3-hydroxybutyric acid esters and filed a patent application on the finding (JP-A-Hei 6-209782). However, the mechanism of the action of these microorganisms has not been clarified. Furthermore, this method enables producing highly optically pure (S)-4-halo-3-hydroxybutyric acid esters, but its product yield is unsatisfactory. When we tried to increase product yield, optical purity was lowered.

SUMMARY OF THE INVENTION

An objective of the present invention is to provide a novel enzyme capable of reducing 4-haloacetoacetic acid esters to produce (S)-4-halo-3-hydroxybutyric acid esters with high optical purity. Another objective of this invention is to provide a method for producing (S)-4-halo-3-hydroxybutyric acid esters with high optical purity using the enzyme.

The present inventors observed the ability of various microorganisms to reduce 4-haloacetoacetic acid esters to produce optically active 4-halo-3-hydroxybutyric acid esters and ardently studied how to isolate an enzyme with such activity from the microorganisms. As a result, the inventors succeeded in isolating the desired enzyme from a microorganism belonging to the genus Kluyveromyces using various purification methods in combination. Furthermore, the present inventors succeeded in producing ethyl (S)-4-halo-3-hydroxybutyrate with high optical purity by reacting the enzyme thus isolated with ethyl 4-haloacetoacetate.

The present invention relates to a novel enzyme capable of reducing 4-haloacetoacetic acid esters to produce (S)-4-halo-3-hydroxybutyric acid esters, and a method for producing (S)-4-halo-3-hydroxybutyric acid esters with high optical purity using that enzyme. More specifically, it relates to:

(1) an enzyme having the following physicochemical properties:
  (a) Function
  The enzyme reduces 4-haloacetoacetic acid esters to produce (S)-4-halo-3-hydroxybutyric acid esters in the presence of β-nicotinamide adenine dinucleotide phosphate (NADPH) as an electron donor;
  (b) Substrate specificity
  The enzyme has high reducing activity on 4-chloro-3-acetoacetic acid esters, but does not act on acetoacetic acid esters. Furthermore, it has no dehydrogenase activity on (S)-4-halo-3-hydroxybutyric acid esters;
  (c) Molecular weight
  The enzyme's molecular weight is about 190,000 dalton when measured by sodium dodecyl sulfate (SDS)-polyacrylamide gel electrophoresis;

(2) the enzyme as described in (1), wherein said enzyme is derived from a microorganism belonging to the genus Kluyveromyces, (3) the enzyme as described in (2), wherein the microorganism belonging to the genus Kluyveromyces is selected from the group consisting of *Kluyveromyces lactis*, *Kluyveromyces marxianus*, *Kluyveromyces polysporus*, *Kluyveromyces aestuarii*, and *Kluyveromyces yarrowii*, (4) the enzyme as described in (2), wherein the microorganism belonging to the genus Kluyveromyces is *Kluyveromyces lactis*, (5) a method for producing the enzyme of (1), wherein said method comprises culturing a microorganism containing said enzyme, and purifying it from the culture, (6) the method as described in (5), wherein said microorganism belongs to the genus Kluyveromyces, (7) the method as described in (5), wherein the purification comprises the steps of treatment with protamine sulfate, extraction from the protamine sulfate precipitates with a solution of a high salt concentration, precipitation with ammonium sulfate, hydrophobic chromatography, and gel filtration, (8) a method for producing (S)-4-halo-3-hydroxybutyric acid esters, wherein said method comprises reacting 4-haloacetoacetic acid esters with the enzyme of (1) and recovering (S)-4-halo-3-hydroxybutyric acid esters, and (9) the method as described in (8), wherein 4-haloacetoacetic acid esters are 4-chloroacetoacetic acid esters and (S)-4-halo-3-hydroxybutyric acid esters are (S)-4-chloro-3-hydroxybutyric acid esters.

DETAILED DESCRIPTION OF THE INVENTION

Figure 1:
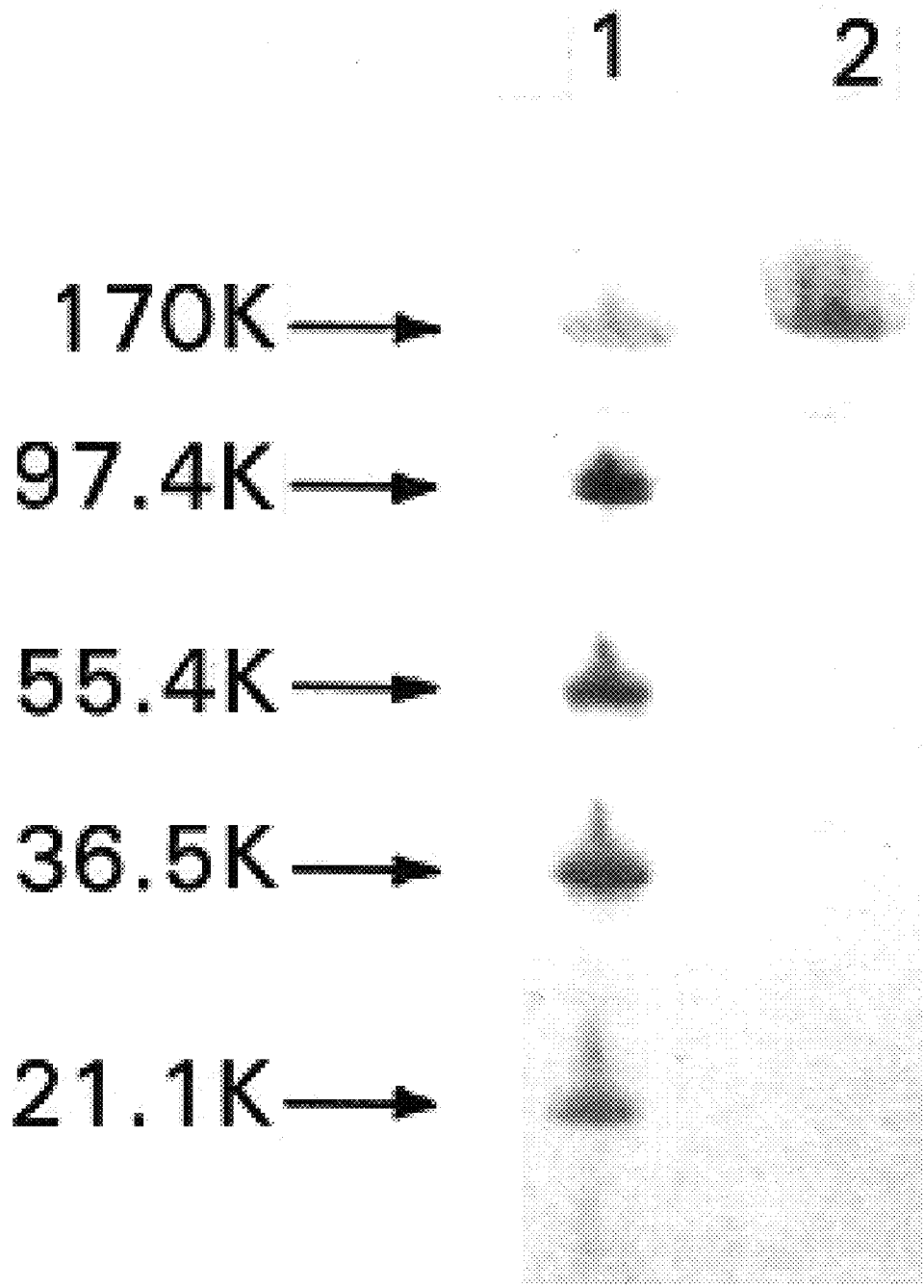
FIG. 1 is shows SDS-polyacrylamide gel electrophoretic patterns. Lane 1 represents the molecular weight markers, and lane 2, the enzyme obtained in Example 1.

The present invention relates to a novel enzyme that reduces 4-haloacetoacetic acid esters to produce (S)-4-halo-3-hydroxybutyric acid esters.

The enzyme of the present invention is characterized by (1) reducing 4-haloacetoacetic acid esters to produce (S)-4-halo-3-hydroxybutyric acid esters in the presence of nicotinamide adenine dinucleotide phosphate (NADPH) as an electron donor; (2) having a high reducing activity on 4-chloroacetoacetic acid esters, having no activity on acetoacetic acid esters, and having no dehydrogenase activity on (S)-4-halo-3-hydroxybutyric acid esters; and (3) having a molecular weight of about 190,000 dalton when measured by SDS-polyacrylamide gel electrophoresis. In addition to the above-described characteristics, the enzyme derived from *Kluyveromyces lactis* isolated by the present inventors has the following properties: (1) its optimal pH is 6.5; (2) it is relatively stable in pH values from 6 to 8; (3) its optimal reaction temperature is 45° C.; (4) it is relatively stable up to 37° C.; and (5) it is completely inhibited by chloromercuribenzoic acid (PCMB), which is an SH reagent, and inhibited by N-ethylmaleimide and methyl vinyl ketone as well as heavy metals such as mercuric chloride, copper sulfate, or zinc sulfate.

The enzyme of this invention can be prepared by culturing microorganisms having the said enzyme, and purifying it from the culture. The microorganisms used for preparing the enzyme of this invention are preferably those belonging to the genus Kluyveromyces, and more preferably those belonging to the species *Kluyveromyces lactis, Kluyveromyces marxianus, Kluyveromyces polysporus, Kluyveromyces aestuarii*, and *Kluyveromyces yarrowii*. Specific strains belonging to these species are exemplified by Kluyveromyces lactis NRIC 1329, *Kluyveromyces lactis* IFO 1673, *Kluyveromyces lactis* CBS 743, *Kluyveromyces marxianus* DSM 70801, *Kluyveromyces polysporus* DSM 70294, *Kluyveromyces aestuarii* IFO 10597, and *Kluyveromyces yarrowii* IFO 10314, but are not construed to be limited thereto.

The above microorganism with NRIC number is recited in NRIC catalogue of Strains, 2nd ed. (1992) published by NODAI Culture Collection, Tokyo University of Agriculture and is available from the same depository. The above microorganisms with IFO numbers are recited in List of Cultures 10th ed. (1996) published by Institute of Fermentation, Osaka (IFO) and are available from IFO. The above microorganism with CBS number is recited in List of Cultures, Fungi and Yeasts, 33rd ed. (1994) published by Centraalbureau voor Schimmelcultures Baarn (CBS)-DELFT (The Netherlands) and is available from CBS. The above microorganisms with DSM number is recited in the Catalogue of Strains (1989) published by "Deutsche Sammlung von Mikroorganismen und Zellkulturen GmbH (DSM)" and can be obtained from DSM.

The microorganisms can be cultured in a medium containing appropriate commonly used components for culture media in combination at 10 to 40° C., preferably 20 to 40° C., with or without shaking. A microorganism belonging to the genus Kluyveromyces can be cultivated in any medium suitable for yeast, for example, a YM medium (pH 6.0) containing glucose (20 g/l), yeast extract (0.3%), and malt extract (0.3%) is preferably used.

The enzyme of this invention can be purified from the culture of microorganisms by an appropriate combination of methods well known in the art. These methods include fractionation of proteins based on their solubility (including precipitation with organic solvents and salting-out with ammonium sulfate); cation exchange chromatography; anion exchange chromatography; gel filtration; hydrophobic chromatography; and affinity chromatography using chelates, pigments, or antibodies. For example, cultured microbial cells can be subjected to disruption, treatment with protamine sulfate, extraction from the protamine sulfate precipitates with a solution of a high salt concentration, precipitation with ammonium sulfate, hydrophobic chromatography on ButylToyopearl, and gel filtration on TSKG 3000SW. By this procedure, the enzyme can be purified to the extent that an almost single protein band can be obtained by polyacrylamide gel electrophoresis.

Once a purified enzyme is obtained, a DNA encoding the said enzyme can be obtained by methods well known in the art. For example, the purified enzyme can be directly analyzed by a protein sequencer to determine the amino acid sequence of its N-terminus. In addition, the purified enzyme is restrictedly cleaved by proteases, which restrictedly cleave proteins, such as lysyl endopeptidase or V8 protease. The peptide fragments thus obtained are purified by reverse-phase liquid chromatography or the like followed by analysis of their N-terminus amino acid sequences by a protein sequencer to determine the inner sequence of the enzyme. The DNA encoding the enzyme can be amplified by polymerase chain reaction (PCR) using primer DNAs synthesized based on the amino acid sequences as obtained above and cDNA prepared from mRNA isolated from the microorganism producing the enzyme or chromosomal DNA as a template. A full-length gene encoding the enzyme can be obtained by screening the cDNA library or the chromosomal DNA library prepared from the microorganism producing the enzyme using the thus-obtained DNA fragments as probes.

The present invention also relates to a method for producing ethyl (S)-4-halo-3-hydroxybutyrate using the enzyme of this invention. The production method of this invention comprises reacting the enzyme of this invention with 4-haloacetoacetic acid esters to produce (S)-4-halo-3-hydroxybutyric acid esters. In addition to the purified natural enzyme, the enzyme used in the method of this invention includes an enzyme derived from microorganisms transformed so as to express the enzyme of this invention. The amount of the enzyme used in the reaction is usually 0.001 to 1,000 U/ml. The amount of ethyl 4-haloacetoacetate is usually 0.01 to 50 wt % based on the weight of the reaction mixture. The amount of NADPH is usually 0.001 to 10 mM. The reaction is usually performed at 0 to 80° C., preferably 15 to 40° C., for 0.1 to 100 h, preferably 1 to 20 h, at pH of 5 to 9, preferably 5.5 to 7.5, in a buffer such as potassium phosphate or a mixed solution of a buffer and a solvent such as toluene, hexane, ethyl acetate, butyl acetate, or chloroform (mixing ratio, 1:9 to 9:1). Ethyl (S)-4-halo-3-hydroxybutyrate thus produced can be easily purified by combining methods such as extraction with solvents such as ethyl acetate, methyl isobutyl ketone, or toluene and distillation. NADPH can be regenerated from NADP$^+$ produced during the reducing reaction utilizing the NADP$^+$ reducing capability of microorganisms (such as glycolysis). The NADP$^+$ reducing capability can be enhanced by adding glucose and ethanol to the reaction system. NADPH can also be regenerated by adding microorganisms capable of generating NADPH from NADP$^+$, or their treated products or enzymes, to the reaction system. For example, NADPH can be regenerated using a microorganism containing glucose dehydrogenase and malic dehydrogenase, or its treated products, or purified enzymes thereof.

The present invention provides ethyl 4-haloaetoacetate reductase with a high stereoselectivity. Using this enzyme, (S)-4-halo-3-hydroxybutyric acid esters can be efficiently produced with high optical purity.

The present invention is illustrated in detail below with reference to examples, but is not to be construed to be restricted thereto.

In these examples, the 4-haloacetoacetic acid ester-reducing activity of the enzyme of this invention was determined by allowing it to react in a reaction system containing 50 mM potassium phosphate buffer (pH 6.5), 0.2 mM NADPH, 20 mM ethyl 4-chloroacetoacetate, and the enzyme at 30° C. and measuring the decrease in the absorbance at 340 nm in proportion to the decrease of NADPH. One unit of the enzyme was defined as the amount of the enzyme to catalyze a decrease of 1 $\mu$mol of NADPH per min. Protein was quantitated by the pigment binding method using a protein assay kit manufactured by BioRad.

EXAMPLE 1
Purification of 4-haloacetoacetic Acid Ester Reductase

*Kluyveromyces lactis* strain NRIC 1329 was cultured in a YM medium (containing glucose 24 g, yeast extract 3 g, malt extract 3 g, and bactopeptone 5 g per liter and having pH 6.0). Microbial cells were harvested by centrifugation. The thus-obtained wet cells were disrupted with an ultrahigh-pressure cell disintegrator (Minilabo) and cell debris was removed by centrifugation to obtain the cell-free extract. After protamine sulfate was added to this cell-free extract, the mixture was centrifuged to obtain the precipitate. This precipitate was suspended in an extraction medium (containing 50 mM potassium phosphate buffer (pH 8.0), 0.01% 2-mercaptoethanol, and 1 M sodium chloride) and centrifuged to obtain the supernatant. Ammonium sulfate was added to this supernatant, and the fraction precipitated under 30 to 70% saturation was recovered. After desalting and centrifugation, the precipitate thus obtained was suspended in the extraction medium (containing 50 mM potassium phosphate buffer (pH 8.0), 0.01% 2-mercaptoethanol, and 1 M sodium chloride), and the suspension was centrifuged to obtain the supernatant. This supernatant was then subjected to hydrophobic column chromatography using ButylToyopearl, and the column was eluted with a linear gradient of ammonium sulfate from 30% to 0% saturation to recover the peak fraction with the NADPH-dependent ethyl 4-chloroacetoacetate reducing activity. This fraction was further purified by gel filtration using TSK gel G3000SW.

The NADPH-dependent ethyl 4-chloroacetoacetate reductase preparation thus obtained revealed an almost single protein band on both polyacrylamide gel electrophoresis under undenatured conditions and SDS-polyacrylamide gel electrophoresis. The purification steps are summarized in Table 1. The specific activity of the purified enzyme was 60.5 U/mg protein.

TABLE 1

| Step | Volume (ml) | Protein (mg) | Total activity (U) | Specific activity (U/mg) |
| --- | --- | --- | --- | --- |
| Cell-free extract | 275 | 13,873 | 2,219 | 0.160 |
| Extract from protamine sulfate precipitate | 600 | 6,204 | 1,445 | 0.233 |
| Ammonium sulfate precipitate (0–70%), desalting, and extraction | 600 | 530.7 | 579.6 | 1.092 |
| Butyl Toyopearl | 4.4 | 56.5 | 155.2 | 2.75 |
| TSK G3000SW | 1.0 | 1.2 | 72.6 | 60.5 |

EXAMPLE 2
Molecular Weight Determination of Ethyl 4-chloroacetoacetate Reductase The molecular weight of the enzyme obtained in Example 1 was measured by SDS-polyacrylamide gel electrophoresis and found to be about 190,000 dalton (FIG. 1). The molecular weight of the enzyme was also determined by TDK G3000SW gel filtration. As a result, the enzyme was eluted in the nonabsorbed fraction, indicating that its molecular weight exceeds 500,000 dalton, the exclusion limit of the gel. The enzyme was further subjected to gel filtration using Superdex 200 and eluted also in the nonabsorbed fraction. Its molecular weight was thus presumed to exceed 600,000 dalton.

EXAMPLE 3
Optimal pH of Ethyl 4-chloroacetoacetate Reductase

Figure 2:
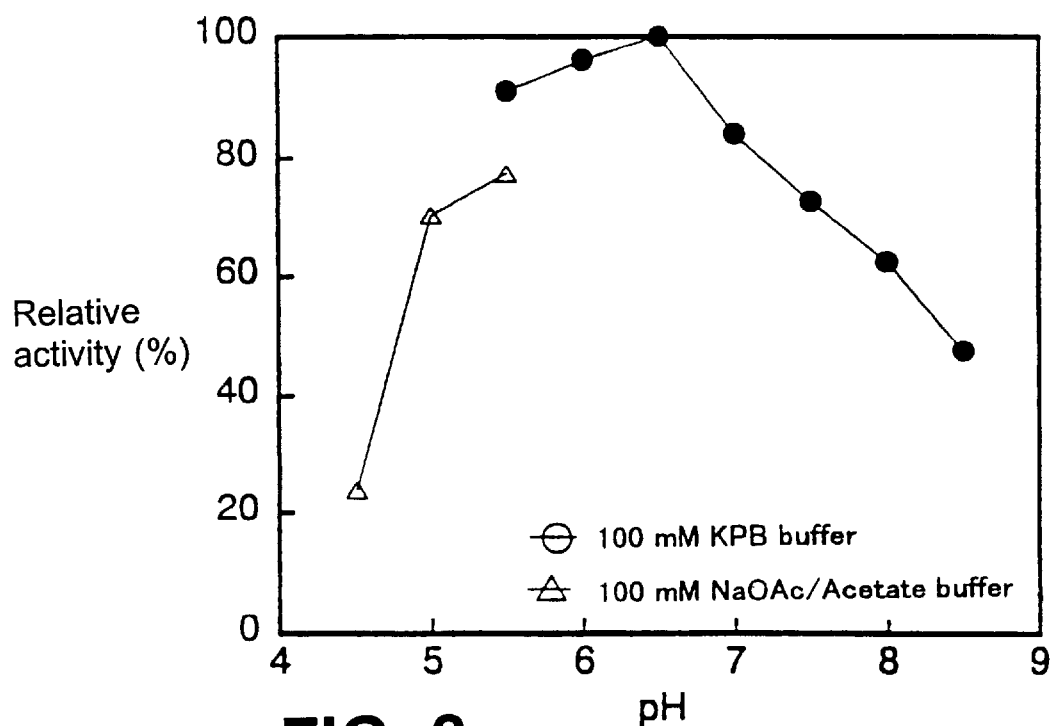
FIG. 2 is a graph showing the pH-dependency of the ethyl 4-chloroacetoacetate reducing activity of the enzyme obtained in Example 1.

The ethyl 4-chloroacetoacetate-reducing activity of the enzyme obtained in Example 1 was assayed at varied pHs that were adjusted with a potassium phosphate buffer or an acetate buffer. The activities are expressed as relative activity taking the maximum activity as 100% and are shown in FIG. 2. The optimum pH for the enzyme reaction was 6.5.

Figure 3:
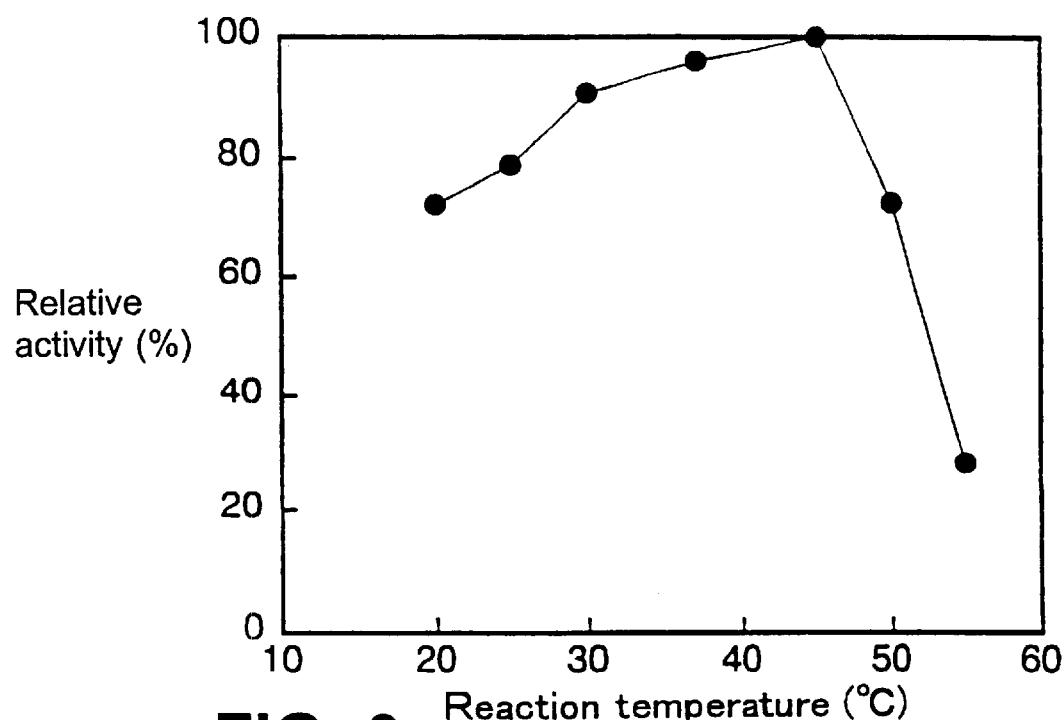
FIG. 3 is a graph showing the temperature dependency of the ethyl 4-chloroacetoacetate reducing activity of the enzyme obtained in Example 1.

EXAMPLE 4
Optimum Reaction Temperature for Ethyl 4-chloroacetoacetate Reductase The ethyl 4-chloroacetoacetate-reducing activity of the enzyme obtained in Example 1 was determined under the standard assay conditions with only the temperature being varied. Results are expressed as relative activity taking the maximum activity as 100% and are shown in FIG. 3. As a result, the optimum reaction temperature for the enzyme was found to be 45° C.

EXAMPLE 5
pH Stability of Ethyl 4-chloroacetoacetate Reductase

Figure 4:
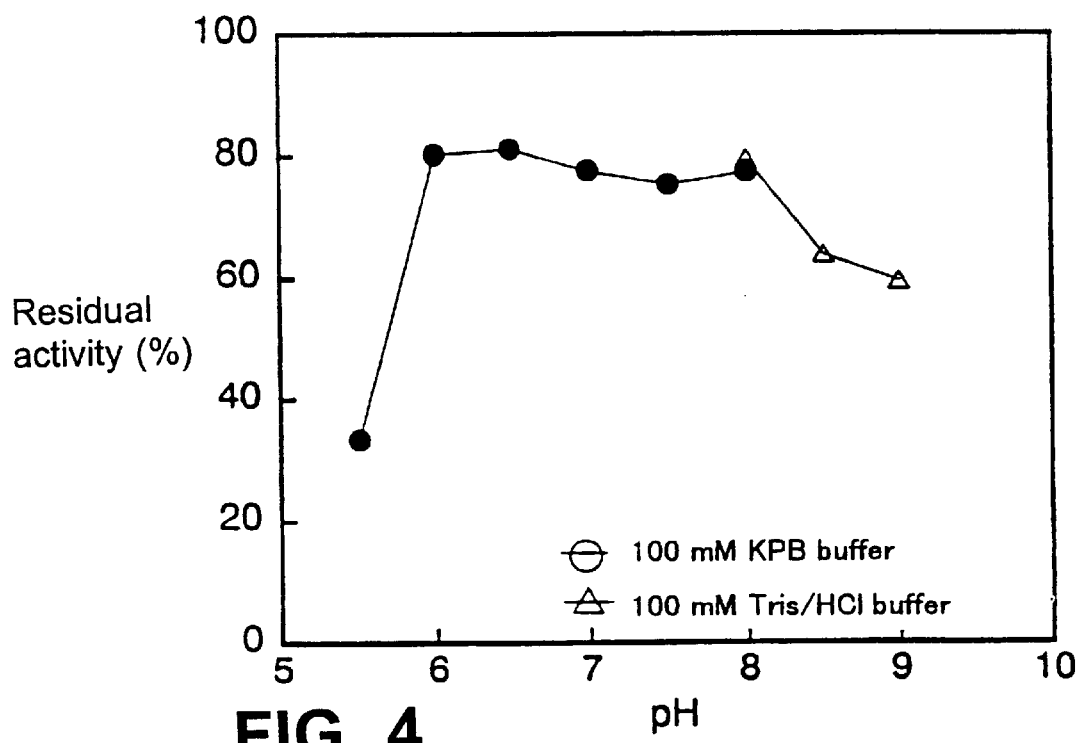
FIG. 4 is a graph showing the residual ethyl 4-chloroacetoacetate reducing activity of the enzyme obtained in Example 1 after it was treated at each pH indicated for 30 min at 30° C.

After the enzyme obtained in Example 1 was incubated in potassium phosphate buffer (pH 5.5 to 8.0) and Tris-HCl buffer (pH 8.0 to 9.0) at 30° C. for 30 min, the ethyl 4-chloroacetoacetate-reducing activity was determined. Results were expressed as residual activity taking the activity under the standard conditions as 100% and are shown in FIG. 4. As a result, the enzyme was found to be most stable at pHs ranging from 6.0 to 8.0.

EXAMPLE 6
Thermostability of Ethyl 4-chloroacetoacetate Reductase

Figure 5:
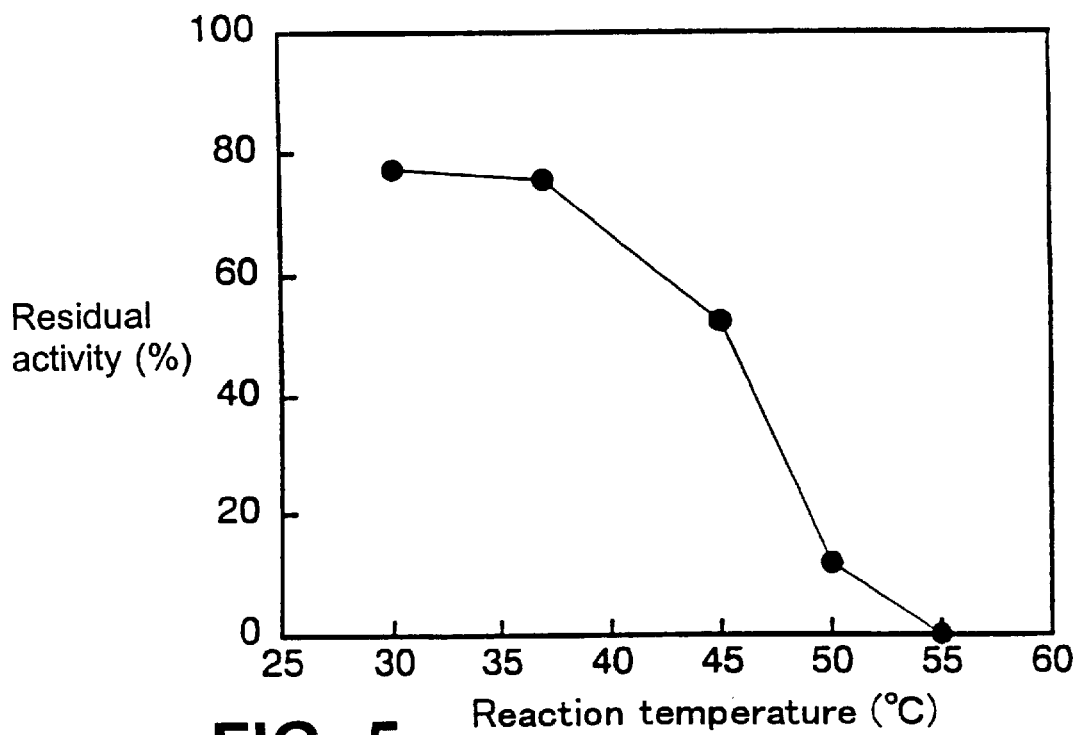
FIG. 5 is a graph showing the residual ethyl 4-chloroacetoacetate reducing activity of the enzyme obtained in Example 1 after it was treated at each temperature indicated for 10 min.

After the enzyme obtained in Example 1 was incubated at pH 7.0 and 37° C., 45° C., 50° C., and 55° C. for 10 min, the ethyl 4-chloroacetoaetate-reducing activity was assayed. Results are expressed as residual activity taking the activity under the standard conditions as 100% and are shown in FIG. 5. As a result, the enzyme was found to show residual activity of 75% or higher of the thermostability under the standard conditions up to 37° C.

EXAMPLE 7

Substrate Specificity of Ethyl 4-chloroacetoacetate Reductase

The reducing activity of the enzyme obtained in Example 1 was measured by reacting the enzyme with various ketones and aldehydes. Results are expressed as relative activity taking the ethyl 4-chloroacetoacetate-reducing activity as 100% and are shown in Table 2.

TABLE 2

| Reagent | Substrate concentration (mM) | Coenzyme | Relative activity (%) |
|---|---|---|---|
| Ethyl 4-chloroacetoacetate | 20 | NADPH | 100 |
| Methyl 4-chloroacetoacetate | 20 | NADPH | 66.3 |
| 2,3-Pentanedione | 20 | NADPH | 44.2 |
| 2,3-Butanedione | 20 | NADPH | 4.2 |
| Propionaldehyde | 20 | NADPH | 0 |
| Acetophenone | 20 | NADPH | 0 |
| 2,4-Pentanedione | 20 | NADPH | 0 |
| Methyl acetoacetate | 20 | NADPH | 0 |
| Ethyl acetoacetate | 20 | NADPH | 0 |
| 4-Hydroxy-2-butanone | 20 | NADPH | 0 |
| Pyridine-3-aldehyde | 20 | NADPH | 0 |
| Acetoxy-2-propanone | 20 | NADPH | 0 |
| Methylglyoxal | 20 | NADPH | 1.8 |
| Xylose | 20 | NADPH | 0 |
| Isatine | 0.4 | NADPH | 0 |
| p-Nitrobenzaldehyde | 0.2 | NADPH | 0 |
| m-Nitrobenzaldehyde | 0.2 | NADPH | 0.4 |
| o-Nitrobenzaldehyde | 0.2 | NADPH | 0 |
| Benzylpyruvic acid | 1 | NADPH | 0 |
| Ethyl 2-oxo-4-phenylacetate | 20 | NADPH | 0 |
| 3-Quinuclidinone | 20 | NADPH | 0.8 |
| Phenylglyoxal | 0.5 | NADPH | 0 |
| Ethyl (S)-4-chloro-3-hydroxy-acetate | 20 | NAD | 0 |
| Ethyl (R)-4-chloro-3-hydroxy-acetate | 20 | NAD | 0 |
| Ethyl 4-chloroacetoaetate | 20 | NADPH | 0 |

As a result, the enzyme was found to show a high activity also with methyl 4-chloroacetoacetate and 2,3-pentanedione as substrate materials.

EXAMPLE 8

Effects of Various Inhibitors on the Activity of Ethyl 4-chloroacetoacetate Reductase After the enzyme obtained in Example 1 was treated with various reagents at 30° C. for 10 min, it was assayed for the remaining activity to reduce ethyl 4chloroacetoacetate. Results are expressed relative to the activity assayed under the standard conditions (100%) as shown in Table 3.

TABLE 3

| Inhibitor | Concentration (mM) | Residual activity (%) |
|---|---|---|
| Phenylmethanesulfonyl fluoride | 1 | 89.4 |
| p-Chloromercuribenzoic acid | 0.05 | 0.0 |
| N-ethylmaleimide | 1 | 20.1 |
| Iodoacetamide | 1 | 53.9 |

TABLE 3-continued

| Inhibitor | Concentration (mM) | Residual activity (%) |
|---|---|---|
| Ethylenediaminetetraacetic acid | 1 | 98.4 |
| o-Phenanthroline | 1 | 88.3 |
| Mercuric chloride | 0.01 | 0.0 |
| Copper sulfate | 1 | 0.0 |
| Zinc sulfate | 1 | 12.2 |
| Chlotonic acid | 50 | 87.7 |
| Methyl vinyl ketone | 10 | 26.3 |
| Quercetin | 0.1 | 68.1 |
| Diethylbarbituric acid | 1 | 82.5 |

As a result, the enzyme was found to be significantly inhibited by p-chloromercuricbenzoic acid, mercuric chloride, and cupric sulfate, and also inhibited by zinc sulfate, N-ethylmaleimide, and methyl vinyl ketone.

EXAMPLE 9

Synthesis of Ethyl (S)-4-Chloro-3-hydroxybutylate using Ethyl 4-chloroacetoacetate Reductase The enzyme obtained in Example 1 (1.8 U), NADPH (21.8 mM), and ethyl 4-chloroacetoacetate (18.2 mM) were added to 1.5 ml of a potassium phosphate buffer (0.1 M, pH 7.0), and the mixture was reacted at 30° C. for 2 h. Ethyl 4-chloro-3-hydroxybutylate with optical purity of 99% ee or higher was thus obtained in the form of comprising S-nantiomer.

Optical purity analysis was performed by extracting 1.0 ml of the reaction solution with ethyl acetate, removing the solvent from the extract, dissolving the residue thus obtained in a mobile phase (0.5 ml) of high-performance liquid chromatography, and subjecting the solution to chromatography with Chiralpak AS (Daicel Chemical) (column, Chiralpak As; mobile phase, hexane/ethanol/isopropyl alcohol/cyclohexanol [92:2.5:1.25:0.25]; flow rate, 1.0 ml/min; temperature, ice-cold; detection, UV 220 nm).

What is claimed is:

1. An enzyme having the following properties:

in the presence of β-nicotinamide adenine dinucleotide phosphate (NADPH) as an electron donor, reduces a 4-haloacetoacetic acid ester to produce a (S)-4-halo-3-hydroxybutyric acid ester;

does not dehydrogenate a (S)-4-halo-3-hydroxybutyric acid ester substrate; and exhibits a molecular weight of about 190,000 daltons when measured by sodium dodecyl sulfate-polyacrylamide gel electrophoresis.

2. The enzyme of claim 1, wherein the enzyme is derived from a species of the genus Kluyveromyces.

3. The enzyme of claim 2, wherein the enzyme is derived from one of the group consisting of *Kluyveromyces lactis, Kluyveromyces marxianus, Kluyveromyces polysporus, Kluyveromyces aestuarii*, and *Kluyveromyces yarrowii*.

4. The enzyme of claim 3, wherein the microorganism is *Kluyveromyces lactis*.

5. The enzyme of claim 1, wherein the 4-haloacetoacetic acid ester is a 4-chloro-3-acetoacetic acid ester.

* * * * *